United States Patent [19]

Rebafka

[11] 4,310,709
[45] Jan. 12, 1982

[54] MANUFACTURE OF BUT-2-EN-1-OL COMPOUNDS BY ISOMERIZING THE CORRESPONDING BUT-3-EN-1-OL COMPOUNDS

[75] Inventor: Walter Rebafka, Eppelheim, Fed. Rep. of Germany

[73] Assignee: BASF Aktiengesellschaft, Fed. Rep. of Germany

[21] Appl. No.: 142,990

[22] Filed: Apr. 23, 1980

Related U.S. Application Data

[63] Continuation of Ser. No. 961,720, Nov. 17, 1978, abandoned.

[30] Foreign Application Priority Data

Nov. 19, 1977 [DE] Fed. Rep. of Germany ....... 2751766

[51] Int. Cl.$^3$ ................. C07C 29/56; C07C 41/32; C07C 45/67; C07C 67/293
[52] U.S. Cl. ................. 568/687; 560/113; 560/122; 568/427; 560/126; 560/179; 568/443; 560/188; 560/189; 568/450; 560/231; 560/261; 568/579; 560/262; 562/466; 568/627; 562/470; 562/471; 568/664; 562/503; 562/508; 568/667; 562/579; 562/588; 568/669; 568/670; 568/673; 568/674; 568/675; 568/686; 568/821; 568/823; 568/825; 568/838; 568/849; 568/850; 568/857; 568/906; 260/405.6; 560/1; 560/55; 560/56; 560/64; 560/73; 560/100; 560/105; 560/106; 560/111; 560/112

[58] Field of Search ............... 560/261, 262, 100, 113, 560/111, 112, 231, 105, 106, 1, 122; 568/627, 669, 667, 686, 675, 838, 673, 821, 823, 825, 579, 849, 850, 857, 664, 906, 687, 670, 450, 427, 443; 562/579, 588, 508, 470, 503, 471, 466; 260/405.6

[56] References Cited

U.S. PATENT DOCUMENTS 3,755,451 8/1973 Kurtz et al. ..................... 560/261
3,922,300 11/1975 Anoda et al. .................... 560/261

FOREIGN PATENT DOCUMENTS 1901709 3/1976 Fed. Rep. of Germany .

OTHER PUBLICATIONS

Tetrahedron, vol. 20, 1964, p. 2911 et seq.
Chemical Communications, 1968, pp. 97–99.
J.A.C.S., 85, 1963, p. 1549.
Canadian Journal of Chemistry, 46, 1968, p. 2225.

Primary Examiner—Vivian Garner
Attorney, Agent, or Firm—Keil & Witherspoon

[57] ABSTRACT

The process for the manufacture of but-2-en-1-ol compounds by isomerizing but-3-en-1-ol compounds in the presence of a palladium catalyst and of hydrogen is improved by modifying the palladium catalyst with selenium or tellurium.

The but-2-en-1-ols manufactured according to the invention are either solvents or valuable starting materials for the manufacture of solvents, dyes, surface coatings, paints and pesticides.

5 Claims, No Drawings

MANUFACTURE OF BUT-2-EN-1-OL COMPOUNDS BY ISOMERIZING THE CORRESPONDING BUT-3-EN-1-OL COMPOUNDS

This is a continuation, of application Ser. No. 961,720 filed Nov. 17, 1978, now abandoned.

The present invention relates to an improved process for the manufacture of but-2-en-1-ol compounds by isomerizing but-3-en-1-ol compounds in the presence of a palladium catalyst modified with selenium or tellurium, and of hydrogen.

Tetrahedron, 20 (1964), 2,911 et seq. discloses that allylcarbinol partially isomerizes to crotyl alcohol in the presence of N-lithium-ethylenediamine as the catalyst. The isomerization of unsaturated alcohols in the presence of a carbonyl of a metal of group 8 of the periodic table as the catalyst has also been disclosed. However, this process has the disadvantage that on isomerization numerous by-products and secondary products, for example the corresponding aldehydes, are obtained (cf. Chem. Comm., 1968, 97–99 and J. Amer. Chem. Soc., 85 (1963), 1,549).

The isomerization can also be carried out purely thermally, without using a catalyst (cf. Can. J. Chem., 46 (1968), 2,225) but this mostly requires the use of very high temperatures, which cause partial resinification of the starting compound.

German Pat. No. 1,901,709 (corresponding to U.S. Pat. No. 3,697,580) describes a process in which the isomerization of a double bond is carried out under the catalytic action of palladium and/or one of its compounds, and hydrogen.

Though the last-mentioned method offers substantial advantages compared to those mentioned earlier, both in operation and in respect of the yields achieved, it is still not entirely satisfactory. On isomerizing a double bond with palladium and hydrogen, hydrogenation results in a greater or lesser amount of the corresponding saturated compound alongside the desired product containing the isomerized double bond.

While minimization of the hydrogenation reactions is desirable because it helps to optimize the yield of the synthesis, there is another compelling reason for wishing to reduce the formation of hydrogenation products. This is the following:

The double bond isomerization of substituted butenols does not result in complete material conversion, but in an equilibrium of the double bond isomers, corresponding to the relative thermodynamic stabilities of the products.

To make the isomerization process economical it is therefore necessary to separate the unconverted starting material from the reaction product by distillation and recycle it to the synthesis.

However, with some butenols removal of the undesired by-product by distillation is impossible, or only possible at disproportionately great expense, because of the insufficient difference in boiling point between unconverted starting material and hydrogenation product. For example, the boiling point of 3-methyl-but-3-en-1-ol is 131.5° C. at 1,020 mbar and that of the corresponding hydrogenation product (3-methyl-butan-1-ol) is 130.9° C.; to take another example, the boiling point of 3-methyl-but-3-en-1-yl acetate is 142.5° C. at 1,020 mbar, whilst that of the corresponding hydrogenation product (isoamyl acetate) is 144° C.

It is thus not possible to differentiate between the unconverted starting material and the hydrogenation product by means of fractional distillation; finer methods of analysis are required.

Since, in the Examples of German Pat. No. 1,901,709, the reaction products were only worked up by distillation, the proportion of hydrogenation product present was not appreciated.

I have found, using suitable methods of analysis, that the application of the process of German Pat. No. 1,901,709 results in substantial amounts of hydrogenation products.

To prevent accumulation of the hydrogenation product on recycling the starting material it is necessary to remove the former as a part-stream, which entails losses of the desired products.

In this procedure, the said losses become less, the lower the amount of hydrogenation product formed per synthesis cycle.

Minimization of the hydrogenation reaction is therefore essential to the economics of the isomerization process.

I have found, surprisingly, that in isomerizing unsaturated compounds in the presence of palladium and/or its compounds and hydrogen, the formation of the hydrogenation by-products can be reduced substantially if the isomerization is carried out in the presence of selenium and/or tellurium and/or one of their compounds as the co-catalyst.

Accordingly, the present invention relates to a process for the manufacture of but-2-en-1-ol compounds of the general formula I

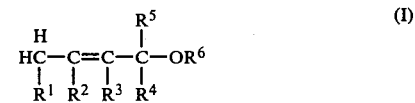

where the individual radicals $R^1$, $R^2$, $R^3$, $R^4$, $R^5$ and $R^6$ may be identical or different and each is hydrogen or an aliphatic radical which may or may not be substituted by OH, OR (where R is an aliphatic radical), halogen or carboxyl, $R^2$ may also be —CHO, $R^2$ and $R^5$ together with the carbon atoms between them may also be members of an alicyclic ring, and/or $R^6$ may also be a cycloaliphatic, araliphatic or aromatic radical or

where $R^7$ is an aliphatic, cycloaliphatic, araliphatic or aromatic radical, by isomerizing but-3-en-1-ol compounds of the general formula II

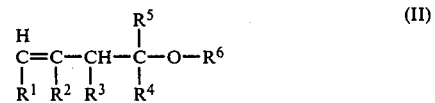

where $R^1$, $R^2$, $R^3$, $R^4$, $R^5$ and $R^6$ have the above meanings, in the presence of palladium and/or one of its compounds, and of hydrogen, at from 0° to 250° C., wherein the isomerization is carried out in the presence of selenium and/or tellurium and/or one of their compounds as the co-catalyst.

Where 3-methyl-but-3-en-1-ol is used, the reaction may be represented by the following equation

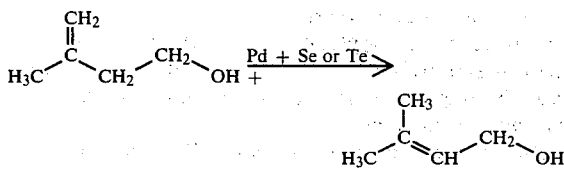

Compared to the conventional processes which have been mentioned, the process of the invention gives the desired but-2-en-1-ol compounds economically, in better yield and greater purity, and with less formation of hydrogenation products, than do the conventional processes.

The starting materials used are but-3-en-1-ols of the general formula II or their esters or ethers. Preferred starting materials II, and accordingly preferred end products I, are those where the individual radicals $R^1$, $R^2$, $R^3$, $R^4$, $R^5$ and $R^6$ are identical or different and each is hydrogen or alkyl of 1 to 6 carbon atoms, which may or may not be substituted by OH, OR, halogen or carboxyl, but preferably each is hydrogen or methyl, as well as those where $R^2$ is —CHO, those where $R^2$ and $R^5$ together with the carbon atoms between them are members of a 5-membered, 6-membered or 7-membered alicyclic ring, and those where $R^6$ is cycloalkyl of 5 to 7 carbon atoms, aralkyl of 7 to 12 carbon atoms, phenyl, naphthyl or

$R^7$ being alkyl of 1 to 6 carbon atoms, cycloalkyl of 5 to 7 carbon atoms, aralkyl of 7 to 12 carbon atoms, phenyl or naphthyl. The said radicals may also be substituted by groups and/or atoms which are inert under the reaction conditions, e.g., ether groups.

Examples of starting materials of the general formula II are but-3-en-1-ol, 3-methyl-but-3-en-1-ol, 4-formyl-but-3-en-1-ol, 3,2,1-trimethyl-but-3-en-1-ol, 2-isobutyl-but-3-en-1-ol, 3-(2'-hydroxyethyl)-but-3-en-1-ol, 1-hexyl-but-3-en-1-ol, 1-methylene-2-methyl-cyclohexan-3-ol, 1-methylene-2-ethyl-cyclopentan-3-ol, 1-methylene-cyclohexan-3-ol, 1-methylene-cycloheptan-3-ol and the corresponding ethyl, cyclohexyl, benzyl, phenyl and α-naphthyl ethers and corresponding esters with acetic acid, cyclohexanecarboxylic acid, benzoic acid, α-naphthoic acid and dihydrocinnamic acid.

The process according to the invention offers particular advantages for the isomerization of 3-methyl-but-3-en-1-ol or its oxygen-substituted derivatives (acetates or ethers) to give prenol or the corresponding prenyl derivatives.

The reaction is carried out in the presence of palladium and/or a palladium compound. Accordingly, examples of suitable isomerization catalysts are palladium black, palladium powder, palladium bromide, arsenide, cyanide, chloride, nitrate, iodide, oxide, sulfide and sulfate, and palladium complex salts, e.g., tetrachloropalladates. The said catalysts may also advantageously be applied to carriers, e.g., active charcoal, barium sulfate, silica gel, alumina or zeolites, in the conventional manner, the resulting supported catalysts being used for the isomerization. Such supported catalysts may be produced by any suitable method, e.g., by impregnating the carrier with appropriate solutions of the palladium salts, by kneading the components together, or by mixing and milling them. For details of the preparation of catalysts, especially supported catalysts, reference may be made to Houben-Weyl, Methoden der Organischen Chemie, volume 4/2, pages 137 et seq. The palladium catalyst is in general used in the form of finely divided palladium metal in an amount of from 0.01 to 5% by weight, preferably from 0.1 to 2% by weight, based on starting material II, or in the form of a finely divided Pd compound in an amount, calculated as palladium, of from 0.01 to 5% by weight, preferably from 0.1 to 2% by weight, based on starting material II.

Advantageous co-catalysts according to the invention are selenium and/or tellurium as the element or as a compound, e.g., selenium dioxide, selenous acid, selenic acid, tellurium dioxide, tellurium trioxide, tellurous acid or o-telluric acid.

The nature of the selenium or tellurium compound employed is not critical, since under the reaction conditions (i.e., in the presence of $H_2$/Pd) the selenium or tellurium compounds of oxidation level greater than 0 are converted to the zero-valency state.

The co-catalyst or co-catalysts is or are employed in an amount of from 1 to 100% by weight, preferably from 2 to 10% by weight, based on metallic palladium.

The method of adding the co-catalyst to the catalyst or to the reaction mixture is not critical. For example, Pd compounds and Se or Te compounds may be conjointly dissolved in the alcohol to be isomerized, and the elements conjointly precipitated with $H_2$; alternatively, the two components can be conjointly applied to a carrier and the supported catalyst thus obtained can, after conventional treatment, be employed for the synthesis; yet again, Te and/or Se and/or their compounds may be subsequently applied to a Pd supported catalyst, or the co-catalyst, in the form of a soluble compound, may be dissolved in the alcohol to be isomerized and the element precipitated during the reaction, by means of hydrogen, onto the previously prepared Pd supported catalyst.

The reaction is carried out in the presence of hydrogen. The hydrogen may be fed to the reaction continuously or batchwise, and/or the catalyst itself may be recharged with hydrogen after a certain reaction time. The hydrogen is in general used in an amount of from 1 to 50 mole % based on starting material II.

The isomerization is as a rule carried out at from 0° to 250° C., preferably from 30° to 150° C., under atmospheric pressure or at superatmospheric pressures of up to 50 atmospheres, continuously or batchwise. Organic solvents which are inert under the reaction conditions, such as ethers, e.g., diethyl ether, dioxan or tetrahydrofuran, alkanols, e.g., ethanol or isobutanol, aromatic or aliphatic hydrocarbons, e.g., heptane or benzene, or mixtures of these, may or may not be used. It is also possible to use solvents which act as hydrogen donors under the reaction conditions and in doing so themselves undergo dehydrogenation, for example cyclohexene derivatives, e.g., cyclohexenol or tetrahydroacetophenone.

To carry out the reaction according to the invention, the starting material of the formula II, the catalyst, the co-catalyst and the inert solvent, if any, are in general kept at the reaction temperature for from about 15 to 360 minutes.

The end product is then separated from the mixture in the conventional manner, for example by fractional distillation.

The compounds obtainable by the process of the invention are either solvents or valuable starting materials for the manufacture of solvents, dyes, surface coatings, paints and pesticides.

The Examples which follow illustrate the advantage of the invention by describing comparative experiments with and without a co-catalyst according to the invention.

EXAMPLE 1

300 g of 3-methyl-but-3-en-1-yl acetate (MBE-ac) were heated for 2 hours at 85° C. in the presence of 0.6 g of a catalyst containing 5% of Pd and 0.25% of Se on active charcoal, with vigorous stirring and whilst passing hydrogen into the mixture. At the intervals of time shown in the Table which follows, the percentage content by weight of MBE-ac in the reaction mixture was determined as an indicator of the progress of the reaction, the percentage content of 3-methyl-butan-1-yl acetate (MBA-ac) was determined as a measure of the formation of undesired hydrogenation product, and the percentage content of the desired product 3-methyl-but-2-en-1-yl acetate (prenyl acetate) was also determined, all determinations being carried out by gas chromatography.

For comparison, the experiment was repeated using a catalyst containing 5% of Pd, but no Se, on active charcoal.

The Table which follows shows the results.

| Time [min] | Isomerization over Pd/Se/C | | | Isomerization over Pd/C (comparative experiment) | | |
|---|---|---|---|---|---|---|
| | MBE-ac [% content] | MBA-ac [% content] | prenyl acetate [% content] | MBE-ac [% content] | MBA-ac [% content] | prenyl acetate [% content] |
| 15 | 42 | 4.5 | 51.1 | 49 | 11 | 37 |
| 30 | 25.5 | 8.5 | 62 | 30 | 17.5 | 50 |
| 45 | 22 | 12 | 63 | 27 | 27 | 54 |
| 60 | 21 | 14 | 61 | 25.5 | 31 | 50 |

EXAMPLE 2

300 g of but-3-en-1-ol were heated for 2 hours at 85° C. in the presence of 0.6 g of a catalyst containing 5% of Pd and 0.25% of Se on active charcoal, with vigorous stirring and whilst passing hydrogen into the mixture; the conversion, the formation of undesired hydrogenation product and the formation of cis-trans-but-2-enols were determined as a function of the reaction time, in the same way as described in Example 1.

For comparison, the experiment was repeated, but using a catalyst containing 5% of Pd but no Se, on active charcoal.

The results are shown in the Table which follows:

| Time [min] | Isomerization over Pd/Se/C | | | (Comparative experiment) Isomerization over Pd/C | | |
|---|---|---|---|---|---|---|
| | but-3-en-1-ol [% content] | butan-1-ol [% content] | cis-trans-but-2-enols [% content] | but-3-en-1-ol [% content] | butan-1-ol [% content] | cis-trans-but-2-enols [% content] |
| 30 | 64 | 4 | 29 | 71 | 6 | 21 |
| 60 | 44 | 7 | 42 | 49 | 12 | 36 |
| 90 | 28.5 | 10 | 57 | 32 | 15.5 | 49 |
| 120 | 27 | 12.5 | 65 | 27.5 | 19 | 59 |

EXAMPLE 3

500 g of 3-methyl-but-3-en-1-ol (MBE) were heated for 2 hours at 85° C. in the presence of 1 g of a catalyst containing 5% of Pd and 0.25% of Se on active charcoal, with vigorous stirring and whilst passing hydrogen into the mixture; the conversion, the formation of undesired hydrogenation product 3-methyl-butanol (MBA) and the formation of prenol were determined as a function of the reaction time, in the same way as described in Example 1.

For comparison, the experiment was repeated, but using a catalyst containing 5% of Pd but no Se, on active charcoal.

The results are shown in the Table which follows.

| Time [min] | Isomerization over Pd/Se/C | | | Isomerization over Pd/C | | |
|---|---|---|---|---|---|---|
| | MBE [% content] | MBA [% content] | prenol [% content] | MBE [% content] | MBA [% content] | prenol [% content] |
| 30 | 52.5 | 1 | 45 | 44.5 | 4 | 50 |
| 60 | 40 | 1.5 | 57 | 35 | 6 | 57 |
| 90 | 32 | 2 | 64 | 31 | 7.5 | 57 |
| 120 | 30 | 2.3 | 62 | 30 | 10.5 | 56.5 |

EXAMPLE 4

500 parts of 3-methyl-but-3-en-1-ol were stirred with 2 parts of a catalyst, containing 4.3% of Pd and 0.9% of Te on an aluminum silicate, for 2 hours at 110° C. in the presence of hydrogen. The conversion of 3-methyl-but-3-en-1-ol was 60%, only 1.8% of 3-methyl-butan-1-ol being formed alongside 55.4% of prenol.

EXAMPLE 5

500 parts of 3-methyl-but-3-en-1-ol were stirred with 1 part of a catalyst, containing 4.4% of Pd and 0.8% of Te on charcoal, for 2 hours at 110° C. in the presence of hydrogen. The conversion of 3-methyl-but-3-en-1-ol was 48%, only 1.7% of 3-methyl-butan-1-ol being formed alongside 46% of prenol.

EXAMPLE 6

2 g of a Pd catalyst containing 5% of Pd on charcoal were introduced into a solution of 2.5 mg of $SeO_2$ in 3-methyl-but-3-en-1-ol (MBE). $H_2$ was passed into the mixture, whilst stirring, for 1 hour at room temperature and then for one hour at 110° C.

The conversion of MBE was 55%, only 2% of 3-methyl-butanol being formed alongside 52% of prenol.

I claim:

1. An improved process for the preparation of but-2-en-1-ol compounds of the general formula I

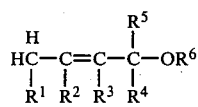

where the individual radicals $R^1$, $R^2$, $R^3$, $R^4$, $R^5$ and $R^6$ may be identical or different and each is hydrogen or an aliphatic radical, which may or may not be substituted by OH, OR (where R is an aliphatic radical), halogen or carboxyl, with the provisos that (1) $R^2$ may also be —CHO, (2) $R^2$ and $R^5$ together with the carbon atoms between them may also be members of an alicyclic ring, and (3) $R^6$ may also be a cycloalkyl of 5 to 7 carbon atoms, aralkyl of 7 to 12 atoms, phenyl, naphthyl or

where $R^7$ is alkyl of 1 to 6 carbon atoms, cycloalkyl of 5 to 7 carbon atoms, aralkyl of 7 to 12 carbon atoms, phenyl or naphthyl, by isomerizing but-3-en-1-ol compounds of the general formula II

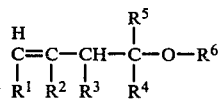

where $R^1$, $R^2$, $R^3$, $R^4$, $R^5$ and $R^6$ have the above meanings, in the presence of palladium and/or one of its compounds, and in the presence of hydrogen, at from 0° to 250° C., wherein the improvement comprises carrying out the isomerization in the presence of selenium and/or tellurium and/or one of their compounds as the co-catalyst.

2. A process as defined in claim 1 wherein the catalyst is supported on a carrier.

3. A process as defined in claim 1 wherein the co-catalyst is employed in an amount of from 2 to 10 percent by weight based on metallic palladium.

4. An improved process for the preparation of but-2-en-1-ol compounds of the general formula I

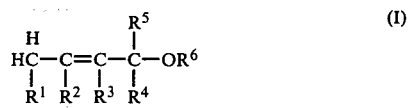

where the individual radicals $R^1$, $R^2$, $R^3$, $R^4$, $R^5$ and $R^6$ may be identical or different and each is hydrogen or alkyl of 1 to 6 carbon atoms, which may or may not be substituted by OH, OR (where R is an aliphatic radical), halogen or carboxyl, with the provisos that (1) $R^2$ may also be —CHO, (2) $R^2$ and $R^5$ together with the carbon atoms between them may also be members of a 5-membered, 6-membered or 7-membered alicyclic ring and (3) $R^6$ may also be cycloalkyl of 5 to 7 carbon atoms, aralkyl of 7 to 12 carbon atoms, phenyl, naphthyl or

where $R^7$ is alkyl of 1 to 6 carbon atoms, cycloalkyl of 5 to 7 carbon atoms, aralkyl of 7 to 12 carbon atoms, phenyl or naphthyl, by isomerizing but-3-en-1-ol compounds of the general formula II

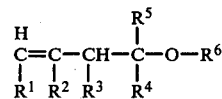

where $R^1$, $R^2$, $R^3$, $R^4$, $R^5$ and $R^6$ have the above meanings, in the presence of palladium and/or one of its compounds, and in the presence of hydrogen, at from 0° to 250° C., wherein the improvement comprises carrying out the isomerization in the presence of selenium and/or tellurium and/or one of their compounds as the co-catalyst.

5. A process as defined in claim 4 wherein in the compound of general formula II the $R^1$, $R^2$, $R^3$, $R^4$, $R^5$ and $R^6$ groups are identical or different and each is hydrogen or methyl.

* * * * *